(12) United States Patent
Pool et al.

(10) Patent No.: US 12,714,477 B2
(45) Date of Patent: Aug. 25, 2026

(54) INTERSPINOUS PROCESS DEVICE AND METHOD

(71) Applicant: NuVasive Specialized Orthopedics, Inc., San Diego, CA (US)

(72) Inventors: Scott Pool, Laguna Hills, CA (US); Arvin Chang, Yorba Linda, CA (US); Peter P. Tran, Irvine, CA (US); Blair Walker, Mission Viejo, CA (US)

(73) Assignee: NuVasive Specialized Orthopedics, Inc., San Diego, PA (US)

( * ) Notice: Subject to any disclaimer, the term of this patent is extended or adjusted under 35 U.S.C. 154(b) by 0 days.

(21) Appl. No.: 18/172,583

(22) Filed: Feb. 22, 2023

(65) Prior Publication Data

US 2023/0248398 A1 Aug. 10, 2023

Related U.S. Application Data

(63) Continuation of application No. 16/597,702, filed on Oct. 9, 2019, now Pat. No. 11,602,380, which is a (Continued)

(51) Int. Cl.

*A61B 17/70* (2006.01)
*A61B 17/00* (2006.01)

(52) U.S. Cl.

CPC ...... *A61B 17/7065* (2013.01); *A61B 17/7056* (2013.01); *A61B 17/7068* (2013.01);

(Continued)

(58) Field of Classification Search

CPC ............ A61B 17/7065; A61B 17/7025; A61B 17/7014–17/7016; A61B 17/7216–17/7225

See application file for complete search history.

(56) References Cited

U.S. PATENT DOCUMENTS

| | | | |
|---|---|---|---|
| 2,702,031 | A | 2/1955 | Wenger |
| 3,111,945 | A | 11/1963 | Von Solbrig |

(Continued)

FOREIGN PATENT DOCUMENTS

| | | | |
|---|---|---|---|
| CN | 1697630 | A | 11/2005 |
| CN | 101040807 | A | 9/2007 |

(Continued)

OTHER PUBLICATIONS

Abe et al., "Experimental external fixation combined with percutaneous discectomy in the management of scoliosis.", SPINE, 1999, pp. 646-653, 24, No. 7.

(Continued)

*Primary Examiner* — Julianna N Harvey

(57) ABSTRACT

An interspinous process device is configured for placement between adjacent spinous processes on a subject's spine. The device includes a housing configured for mounting to a first spinal process, the housing having a lead screw fixedly secured at one end thereof. A magnetic assembly is at least partially disposed within the housing and configured for mounting to a second spinal process. The magnetic assembly includes a hollow magnet configured for rotation within the magnetic assembly, the hollow magnet comprising a threaded insert configured to engage with the lead screw. An externally applied magnetic field rotates the hollow magnet in a first direction or a second, opposite direction. Rotation of the hollow magnet in the first direction causes telescopic movement of the magnetic assembly out of the housing (i.e., elongation) and rotation in the second direction causes telescopic movement of the magnetic assembly into the housing (i.e., shortening).

17 Claims, 11 Drawing Sheets

Related U.S. Application Data continuation of application No. 15/454,899, filed on Mar. 9, 2017, now Pat. No. 10,478,232, which is a continuation of application No. 12/761,141, filed on Apr. 15, 2010, now Pat. No. 9,622,792.

(60) Provisional application No. 61/173,902, filed on Apr. 29, 2009.

(52) U.S. Cl.
CPC ............... *A61B 2017/00022* (2013.01); *A61B 2017/00039* (2013.01); *A61B 2017/00411* (2013.01); *A61B 2017/00876* (2013.01)

(56) References Cited

U.S. PATENT DOCUMENTS 3,372,476 A 3/1968 Peiffer
3,377,576 A 4/1968 Langberg
3,512,901 A 5/1970 Law
3,597,781 A 8/1971 Eibes
3,900,025 A 8/1975 Barnes, Jr.
3,915,151 A 10/1975 Kraus
RE28,907 E 7/1976 Eibes et al.
3,976,060 A 8/1976 Hildebrandt et al.
4,010,758 A 3/1977 Rockland et al.
4,056,743 A 11/1977 Clifford et al.
4,068,821 A 1/1978 Morrison
4,078,559 A 3/1978 Nissinen
4,204,541 A 5/1980 Kapitanov
4,357,946 A 11/1982 Dutcher et al.
4,386,603 A 6/1983 Mayfield
4,448,191 A 5/1984 Rodnyansky et al.
4,486,176 A 12/1984 Tardieu et al.
4,501,266 A 2/1985 McDaniel
4,522,501 A 6/1985 Shannon
4,537,520 A 8/1985 Ochiai et al.
4,550,279 A 10/1985 Klein
4,561,798 A 12/1985 Elcrin et al.
4,573,454 A 3/1986 Hoffman
4,592,355 A 6/1986 Antebi
4,595,007 A 6/1986 Mericle
4,642,257 A 2/1987 Chase
4,658,809 A 4/1987 Ulrich et al.
4,700,091 A 10/1987 Wuthrich
4,747,832 A 5/1988 Buffet
4,854,304 A 8/1989 Zielke
4,904,861 A 2/1990 Epstein et al.
4,931,055 A 6/1990 Bumpus et al.
4,940,467 A 7/1990 Tronzo
4,957,495 A 9/1990 Kluger
4,973,331 A 11/1990 Pursley et al.
5,010,879 A 4/1991 Moriya et al.
5,030,235 A 7/1991 Campbell, Jr.
5,041,112 A 8/1991 Mingozzi et al.
5,064,004 A 11/1991 Lundell
5,074,882 A 12/1991 Grammont et al.
5,092,889 A 3/1992 Campbell, Jr.
5,133,716 A 7/1992 Plaza
5,142,407 A 8/1992 Varaprasad et al.
5,156,605 A 10/1992 Pursley et al.
5,263,955 A 11/1993 Baumgart et al.
5,290,289 A 3/1994 Sanders et al.
5,290,312 A 3/1994 Kojimoto
5,306,275 A 4/1994 Bryan
5,330,503 A 7/1994 Yoon
5,334,202 A 8/1994 Carter
5,336,223 A 8/1994 Rogers
5,356,411 A 10/1994 Spievack
5,356,424 A 10/1994 Buzerak et al.
5,364,396 A 11/1994 Robinson et al.
5,403,322 A 4/1995 Herzenberg et al.
5,429,638 A 7/1995 Muschler et al.
5,437,266 A 8/1995 McPherson et al.
5,466,261 A 11/1995 Richelsoph
5,468,030 A 11/1995 Walling
5,480,437 A 1/1996 Draenert
5,509,888 A 4/1996 Miller
5,516,335 A 5/1996 Kummer et al.
5,527,309 A 6/1996 Shelton
5,536,269 A 7/1996 Spievack
5,549,610 A 8/1996 Russell et al.
5,573,012 A 11/1996 McEwan
5,575,790 A 11/1996 Chen et al.
5,582,616 A 12/1996 Bolduc et al.
5,620,445 A 4/1997 Brosnahan et al.
5,620,449 A 4/1997 Faccioli et al.
5,626,579 A 5/1997 Muschler et al.
5,626,613 A 5/1997 Schmieding
5,632,744 A 5/1997 Campbell, Jr.
5,659,217 A 8/1997 Petersen
5,662,683 A 9/1997 Kay
5,672,175 A 9/1997 Martin
5,672,177 A 9/1997 Seldin
5,676,665 A 10/1997 Bryan
5,700,263 A 12/1997 Schendel
5,704,938 A 1/1998 Staehlin et al.
5,704,939 A 1/1998 Justin
5,720,746 A 2/1998 Soubeiran
5,743,910 A 4/1998 Bays et al.
5,762,599 A 6/1998 Sohn
5,771,903 A 6/1998 Jakobsson
5,810,815 A 9/1998 Morales
5,827,286 A 10/1998 Incavo et al.
5,830,221 A 11/1998 Stein et al.
5,879,375 A 3/1999 Larson, Jr. et al.
5,902,304 A 5/1999 Walker et al.
5,935,127 A 8/1999 Border
5,945,762 A 8/1999 Chen et al.
5,961,553 A 10/1999 Coty et al.
5,976,138 A 11/1999 Baumgart et al.
5,979,456 A 11/1999 Magovern
6,022,349 A * 2/2000 McLeod ............... A61B 17/66 606/58
6,033,412 A 3/2000 Losken et al.
6,034,296 A 3/2000 Elvin et al.
6,102,922 A 8/2000 Jakobsson et al.
6,106,525 A 8/2000 Sachse
6,126,660 A 10/2000 Dietz
6,126,661 A 10/2000 Faccioli et al.
6,126,664 A 10/2000 Troxell et al.
6,138,681 A 10/2000 Chen et al.
6,139,316 A 10/2000 Sachdeva et al.
6,162,223 A 12/2000 Orsak et al.
6,183,476 B1 2/2001 Gerhardt et al.
6,200,317 B1 3/2001 Aalsma et al.
6,234,956 B1 5/2001 He et al.
6,241,730 B1 6/2001 Alby
6,245,075 B1 6/2001 Betz et al.
6,315,784 B1 11/2001 Djurovic
6,319,255 B1 11/2001 Grundei et al.
6,331,744 B1 12/2001 Chen et al.
6,336,929 B1 1/2002 Justin
6,343,568 B1 2/2002 McClasky
6,358,283 B1 3/2002 Hogfors et al.
6,375,682 B1 4/2002 Fleischmann et al.
6,389,187 B1 5/2002 Greenaway et al.
6,400,980 B1 6/2002 Lemelson
6,402,753 B1 6/2002 Cole et al.
6,409,175 B1 6/2002 Evans et al.
6,416,516 B1 7/2002 Stauch et al.
6,417,750 B1 7/2002 Sohn
6,499,907 B1 12/2002 Baur
6,500,110 B1 12/2002 Davey et al.
6,508,820 B2 1/2003 Bales
6,510,345 B1 1/2003 Van Bentem
6,537,196 B1 3/2003 Creighton, IV et al.
6,554,831 B1 4/2003 Rivard et al.
6,565,573 B1 5/2003 Ferrante et al.
6,565,576 B1 5/2003 Stauch et al.
6,582,313 B2 6/2003 Perrow
6,583,630 B2 6/2003 Mendes et al.
6,616,669 B2 9/2003 Ogilvie et al.
6,626,917 B1 9/2003 Craig

(56) References Cited

U.S. PATENT DOCUMENTS 6,656,135 B2 12/2003 Zogbi et al.
6,656,194 B1 12/2003 Gannoe et al.
6,667,725 B1 12/2003 Simons et al.
6,673,079 B1 1/2004 Kane
6,702,816 B2 3/2004 Buhler
6,706,042 B2 3/2004 Taylor
6,709,293 B2 3/2004 Mori et al.
6,730,087 B1 5/2004 Butsch
6,761,503 B2 7/2004 Breese
6,769,499 B2 8/2004 Cargill et al.
6,789,442 B2 9/2004 Forch
6,796,984 B2 9/2004 Soubeiran
6,802,844 B2 10/2004 Ferree
6,809,434 B1 10/2004 Duncan et al.
6,835,207 B2 12/2004 Zacouto et al.
6,849,076 B2 2/2005 Blunn et al.
6,852,113 B2 2/2005 Nathanson et al.
6,918,838 B2 7/2005 Schwarzler et al.
6,918,910 B2 7/2005 Smith et al.
6,921,400 B2 7/2005 Sohngen
6,923,951 B2 8/2005 Contag et al.
6,971,143 B2 12/2005 Domroese
7,001,346 B2 2/2006 White
7,008,425 B2 3/2006 Phillips
7,011,658 B2 3/2006 Young
7,029,472 B1 4/2006 Fortin
7,029,475 B2 4/2006 Panjabi
7,041,105 B2 5/2006 Michelson
7,060,080 B2 6/2006 Bachmann
7,063,706 B2 6/2006 Wittenstein
7,105,029 B2 9/2006 Doubler et al.
7,105,968 B2 9/2006 Nissen
7,114,501 B2 10/2006 Johnson et al.
7,115,129 B2 10/2006 Heggeness
7,135,022 B2 11/2006 Kosashvili et al.
7,160,312 B2 1/2007 Saadat
7,163,538 B2 1/2007 Altarac et al.
7,189,005 B2 3/2007 Ward
7,191,007 B2 3/2007 Desai et al.
7,218,232 B2 5/2007 DiSilvestro et al.
7,238,191 B2 7/2007 Bachmann
7,241,300 B2 7/2007 Sharkawy et al.
7,243,719 B2 7/2007 Baron et al.
7,255,682 B1 8/2007 Bartol, Jr. et al.
7,282,023 B2 10/2007 Frering
7,285,087 B2 10/2007 Moaddeb et al.
7,302,015 B2 11/2007 Kim et al.
7,302,858 B2 12/2007 Walsh et al.
7,314,443 B2 1/2008 Jordan et al.
7,333,013 B2 2/2008 Berger
7,357,037 B2 4/2008 Hnat et al.
7,357,632 B1 4/2008 Belfor et al.
7,357,635 B2 4/2008 Belfor et al.
7,360,542 B2 4/2008 Nelson et al.
7,390,007 B2 6/2008 Helms et al.
7,390,294 B2 6/2008 Hassler, Jr.
7,402,134 B2 7/2008 Moaddeb et al.
7,402,176 B2 7/2008 Malek
7,429,259 B2 9/2008 Cadeddu et al.
7,445,010 B2 11/2008 Kugler et al.
7,458,981 B2 12/2008 Fielding et al.
7,485,149 B1 2/2009 White
7,489,495 B2 2/2009 Stevenson
7,530,981 B2 5/2009 Kutsenko
7,531,002 B2 5/2009 Sutton et al.
7,553,298 B2 6/2009 Hunt et al.
7,561,916 B2 7/2009 Hunt et al.
7,601,156 B2 10/2009 Robinson
7,608,104 B2 10/2009 Yuan et al.
7,611,526 B2 11/2009 Carl et al.
7,618,435 B2 11/2009 Opolski
7,658,754 B2 2/2010 Zhang et al.
7,666,184 B2 2/2010 Stauch
7,666,210 B2 2/2010 Franck et al.
7,678,136 B2 3/2010 Doubler et al.
7,678,139 B2 3/2010 Garamszegi et al.
7,708,737 B2 5/2010 Kraft et al.
7,708,762 B2 5/2010 McCarthy et al.
7,727,143 B2 6/2010 Birk et al.
7,753,913 B2 7/2010 Szakelyhidi, Jr. et al.
7,753,915 B1 7/2010 Eksler et al.
7,762,998 B2 7/2010 Birk et al.
7,763,080 B2 7/2010 Southworth
7,766,855 B2 8/2010 Miethke
7,775,215 B2 8/2010 Hassler, Jr. et al.
7,776,068 B2 8/2010 Ainsworth et al.
7,776,075 B2 8/2010 Bruneau et al.
7,776,091 B2 8/2010 Mastrorio et al.
7,787,958 B2 8/2010 Stevenson
7,794,476 B2 9/2010 Wisnewski
7,811,328 B2 10/2010 Molz, IV et al.
7,835,779 B2 11/2010 Anderson et al.
7,837,691 B2 11/2010 Cordes et al.
7,862,502 B2 1/2011 Pool et al.
7,862,586 B2 1/2011 Malek
7,867,235 B2 1/2011 Fell et al.
7,875,033 B2 1/2011 Richter et al.
7,887,566 B2 2/2011 Hynes
7,901,381 B2 3/2011 Birk et al.
7,909,852 B2 3/2011 Boomer et al.
7,918,844 B2 4/2011 Byrum et al.
7,938,841 B2 5/2011 Sharkawy et al.
7,955,357 B2 6/2011 Kiester
7,981,025 B2 7/2011 Pool et al.
7,985,256 B2 7/2011 Grotz et al.
7,988,709 B2 8/2011 Clark et al.
8,002,809 B2 8/2011 Baynham
8,011,308 B2 9/2011 Picchio
8,034,080 B2 10/2011 Malandain et al.
8,043,299 B2 10/2011 Conway
8,043,338 B2 10/2011 Dant
8,057,472 B2 11/2011 Walker et al.
8,057,473 B2 11/2011 Orsak et al.
8,057,513 B2 11/2011 Kohm et al.
8,083,741 B2 12/2011 Morgan et al.
8,092,499 B1 1/2012 Roth
8,095,317 B2 1/2012 Ekseth et al.
8,105,360 B1 1/2012 Connor
8,105,363 B2 1/2012 Fielding et al.
8,114,158 B2 2/2012 Carl et al.
8,123,805 B2 2/2012 Makower et al.
8,133,280 B2 3/2012 Voellmicke et al.
8,147,517 B2 4/2012 Trieu et al.
8,147,549 B2 4/2012 Metcalf, Jr. et al.
8,162,897 B2 4/2012 Byrum
8,162,979 B2 4/2012 Sachs et al.
8,177,789 B2 5/2012 Magill et al.
8,197,490 B2 6/2012 Pool et al.
8,211,149 B2 7/2012 Justis
8,211,151 B2 7/2012 Schwab et al.
8,211,179 B2 7/2012 Molz, IV et al.
8,216,275 B2 7/2012 Fielding et al.
8,221,420 B2 7/2012 Keller
8,226,690 B2 7/2012 Altarac et al.
8,236,002 B2 8/2012 Fortin et al.
8,241,331 B2 8/2012 Arnin
8,246,533 B2 8/2012 Chang et al.
8,246,630 B2 8/2012 Manzi et al.
8,252,063 B2 8/2012 Stauch
8,267,969 B2 9/2012 Altarac et al.
8,278,941 B2 10/2012 Kroh et al.
8,282,671 B2 10/2012 Connor
8,298,240 B2 10/2012 Giger et al.
8,323,290 B2 12/2012 Metzger et al.
8,357,182 B2 1/2013 Seme
8,366,628 B2 2/2013 Denker et al.
8,372,078 B2 2/2013 Collazo
8,386,018 B2 2/2013 Stauch et al.
8,394,124 B2 3/2013 Biyani
8,403,958 B2 3/2013 Schwab
8,414,584 B2 4/2013 Brigido
8,419,801 B2 4/2013 DiSilvestro et al.
8,425,608 B2 4/2013 Dewey et al.
8,435,268 B2 5/2013 Thompson et al.

(56) References Cited

U.S. PATENT DOCUMENTS 8,439,915 B2 5/2013 Harrison et al.
8,439,926 B2 5/2013 Bojarski et al.
8,444,693 B2 5/2013 Reiley
8,469,908 B2 6/2013 Asfora
8,470,004 B2 6/2013 Reiley
8,486,070 B2 7/2013 Morgan et al.
8,486,076 B2 7/2013 Chavarria et al.
8,486,110 B2 7/2013 Fielding et al.
8,486,147 B2 7/2013 De Villiers et al.
8,494,805 B2 7/2013 Roche et al.
8,496,662 B2 7/2013 Novak et al.
8,518,062 B2 8/2013 Cole et al.
8,523,866 B2 9/2013 Sidebotham et al.
8,529,474 B2 9/2013 Gupta et al.
8,529,606 B2 9/2013 Alamin et al.
8,529,607 B2 9/2013 Alamin et al.
8,556,901 B2 10/2013 Anthony et al.
8,556,911 B2 10/2013 Mehta et al.
8,556,975 B2 10/2013 Ciupik et al.
8,562,653 B2 10/2013 Alamin et al.
8,568,457 B2 10/2013 Hunziker
8,579,979 B2 11/2013 Edie et al.
8,585,595 B2 11/2013 Heilman
8,585,740 B1 11/2013 Ross et al.
8,591,549 B2 11/2013 Lange
8,591,553 B2 11/2013 Eisermann et al.
8,613,758 B2 12/2013 Linares
8,617,220 B2 12/2013 Skaggs
8,623,036 B2 1/2014 Harrison et al.
8,632,544 B2 1/2014 Haaja et al.
8,632,548 B2 1/2014 Soubeiran
8,632,563 B2 1/2014 Nagase et al.
8,636,771 B2 1/2014 Butler et al.
8,636,802 B2 1/2014 Serhan et al.
8,641,719 B2 2/2014 Gephart et al.
8,641,723 B2 2/2014 Connor
8,657,856 B2 2/2014 Gephart et al.
8,663,285 B2 3/2014 Dall et al.
8,663,287 B2 3/2014 Butler et al.
8,668,719 B2 3/2014 Alamin et al.
8,709,090 B2 4/2014 Makower et al.
8,758,347 B2 6/2014 Weiner et al.
8,758,355 B2 6/2014 Fisher et al.
8,771,272 B2 7/2014 LeCronier et al.
8,777,947 B2 7/2014 Zahrly et al.
8,777,995 B2 7/2014 McClintock et al.
8,790,343 B2 7/2014 McClellan et al.
8,790,409 B2 7/2014 Van den Heuvel et al.
8,828,058 B2 9/2014 Elsebaie et al.
8,828,087 B2 9/2014 Stone et al.
8,840,651 B2 9/2014 Reiley
8,870,881 B2 10/2014 Rezach et al.
8,870,959 B2 10/2014 Arnin
8,894,663 B2 11/2014 Giger et al.
8,915,915 B2 12/2014 Harrison et al.
8,915,917 B2 12/2014 Doherty et al.
8,920,422 B2 12/2014 Homeier et al.
8,945,188 B2 2/2015 Rezach et al.
8,961,521 B2 2/2015 Keefer et al.
8,961,567 B2 2/2015 Hunziker
8,968,402 B2 3/2015 Myers et al.
8,968,406 B2 3/2015 Armin
8,992,527 B2 3/2015 Guichet
9,022,917 B2 5/2015 Kasic et al.
9,044,218 B2 6/2015 Young
9,060,810 B2 6/2015 Kercher et al.
9,078,703 B2 7/2015 Arnin
9,622,792 B2 4/2017 Pool et al.
9,730,612 B2 * 8/2017 Quick ................. H01F 27/2823
10,478,232 B2 11/2019 Pool et al.
2002/0050112 A1 5/2002 Koch et al.
2002/0072758 A1 6/2002 Reo et al.
2002/0164905 A1 11/2002 Bryant
2003/0040671 A1 2/2003 Somogyi et al.
2003/0144669 A1 7/2003 Robinson
2003/0220643 A1 11/2003 Ferree
2003/0220644 A1 11/2003 Thelen et al.
2004/0011137 A1 1/2004 Hnat et al.
2004/0011365 A1 1/2004 Govari et al.
2004/0019353 A1 1/2004 Freid et al.
2004/0023623 A1 2/2004 Stauch et al.
2004/0030395 A1 2/2004 Blunn et al.
2004/0055610 A1 3/2004 Forsell
2004/0133219 A1 7/2004 Forsell
2004/0138725 A1 7/2004 Forsell
2004/0193266 A1 9/2004 Meyer
2005/0034705 A1 2/2005 McClendon
2005/0049617 A1 3/2005 Chatlynne et al.
2005/0065529 A1 3/2005 Liu et al.
2005/0090823 A1 4/2005 Bartimus
2005/0096744 A1 5/2005 Trieu
2005/0159754 A1 7/2005 Odrich
2005/0234448 A1 10/2005 McCarthy
2005/0234462 A1 10/2005 Hershberger
2005/0244499 A1 11/2005 Diaz et al.
2005/0246034 A1 11/2005 Soubeiran
2005/0261779 A1 11/2005 Meyer
2005/0272976 A1 12/2005 Tanaka et al.
2006/0004459 A1 1/2006 Hazebrouck et al.
2006/0009767 A1 1/2006 Kiester
2006/0036259 A1 2/2006 Carl et al.
2006/0036323 A1 2/2006 Carl et al.
2006/0036324 A1 2/2006 Sachs et al.
2006/0047282 A1 * 3/2006 Gordon .............. A61B 17/7016
606/907
2006/0058792 A1 3/2006 Hynes
2006/0069447 A1 3/2006 DiSilvestro et al.
2006/0074448 A1 4/2006 Harrison et al.
2006/0079897 A1 4/2006 Harrison et al.
2006/0136062 A1 6/2006 DiNello et al.
2006/0142767 A1 6/2006 Green et al.
2006/0155279 A1 7/2006 Ogilvie
2006/0195087 A1 8/2006 Sacher et al.
2006/0195088 A1 8/2006 Sacher et al.
2006/0200134 A1 9/2006 Freid et al.
2006/0204156 A1 9/2006 Takehara et al.
2006/0235299 A1 10/2006 Martinelli
2006/0235424 A1 10/2006 Vitale et al.
2006/0241601 A1 10/2006 Tautwein et al.
2006/0241614 A1 10/2006 Bruneau et al.
2006/0241746 A1 10/2006 Shaoulian et al.
2006/0241767 A1 10/2006 Doty
2006/0249914 A1 11/2006 Dulin
2006/0271107 A1 11/2006 Harrison et al.
2006/0282073 A1 12/2006 Simanovsky
2006/0293662 A1 12/2006 Boyer
2006/0293683 A1 12/2006 Stauch
2007/0010814 A1 1/2007 Stauch
2007/0010887 A1 1/2007 Williams et al.
2007/0021644 A1 1/2007 Woolson et al.
2007/0031131 A1 2/2007 Griffitts
2007/0043376 A1 2/2007 Leatherbury et al.
2007/0050030 A1 3/2007 Kim
2007/0093823 A1 4/2007 Booth et al.
2007/0118215 A1 5/2007 Moaddeb
2007/0156237 A1 * 7/2007 Kwak .................. A61F 2/4405
623/13.14
2007/0161984 A1 7/2007 Cresina et al.
2007/0173826 A1 7/2007 Canaveral et al.
2007/0173837 A1 7/2007 Chan et al.
2007/0179493 A1 8/2007 Kim
2007/0185374 A1 8/2007 Kick et al.
2007/0213751 A1 9/2007 Scirica et al.
2007/0213781 A1 9/2007 Scirica et al.
2007/0233098 A1 10/2007 Mastrorio et al.
2007/0239159 A1 10/2007 Altarac et al.
2007/0239161 A1 10/2007 Giger et al.
2007/0255088 A1 11/2007 Jacobson et al.
2007/0255413 A1 11/2007 Edie et al.
2007/0264605 A1 11/2007 Belfor et al.

(56) References Cited

U.S. PATENT DOCUMENTS

2007/0270803 A1 11/2007 Giger et al.
2007/0276368 A1* 11/2007 Trieu ................ A61B 17/7065 606/86 A
2007/0276369 A1* 11/2007 Allard .................... A61F 2/442 606/86 A
2007/0276373 A1 11/2007 Malandain
2007/0276378 A1 11/2007 Harrison et al.
2007/0276493 A1 11/2007 Malandain et al.
2007/0288024 A1 12/2007 Gollogly
2007/0288183 A1 12/2007 Bulkes et al.
2008/0009792 A1 1/2008 Henniges et al.
2008/0015577 A1 1/2008 Loeb
2008/0021454 A1 1/2008 Chao et al.
2008/0021455 A1 1/2008 Chao et al.
2008/0021456 A1 1/2008 Gupta et al.
2008/0027435 A1 1/2008 Zucherman et al.
2008/0027436 A1 1/2008 Cournoyer et al.
2008/0033431 A1 2/2008 Jung et al.
2008/0033436 A1 2/2008 Song et al.
2008/0039943 A1 2/2008 Le Couedic
2008/0051784 A1 2/2008 Gollogly
2008/0051800 A1 2/2008 Diaz et al.
2008/0082118 A1 4/2008 Edidin et al.
2008/0086128 A1 4/2008 Lewis
2008/0097188 A1 4/2008 Pool et al.
2008/0097487 A1 4/2008 Pool et al.
2008/0097496 A1 4/2008 Chang et al.
2008/0108995 A1 5/2008 Conway et al.
2008/0161933 A1 7/2008 Grotz et al.
2008/0167685 A1 7/2008 Allard et al.
2008/0167686 A1 7/2008 Allard et al.
2008/0172063 A1 7/2008 Taylor
2008/0172072 A1 7/2008 Pool et al.
2008/0177319 A1 7/2008 Schwab
2008/0177326 A1 7/2008 Thompson
2008/0190237 A1 8/2008 Radinger et al.
2008/0228186 A1 9/2008 Gall et al.
2008/0255615 A1 10/2008 Vittur et al.
2008/0272928 A1 11/2008 Shuster
2008/0275557 A1 11/2008 Makower et al.
2009/0030462 A1 1/2009 Buttermann
2009/0076597 A1 3/2009 Dahlgren et al.
2009/0082815 A1 3/2009 Zylber et al.
2009/0082820 A1 3/2009 Fielding et al.
2009/0088803 A1 4/2009 Justis et al.
2009/0093820 A1 4/2009 Trieu et al.
2009/0093890 A1 4/2009 Gelbart
2009/0112207 A1 4/2009 Walker et al.
2009/0112262 A1 4/2009 Pool et al.
2009/0112263 A1* 4/2009 Pool .................... A61B 17/707 600/587
2009/0125062 A1 5/2009 Arnin
2009/0163780 A1 6/2009 Tieu
2009/0171356 A1 7/2009 Klett
2009/0192514 A1 7/2009 Feinberg et al.
2009/0198144 A1 8/2009 Phillips et al.
2009/0216113 A1 8/2009 Meier et al.
2009/0248079 A1* 10/2009 Kwak ................ A61B 17/7065 606/248
2009/0248148 A1 10/2009 Shaolian et al.
2009/0264929 A1 10/2009 Alamin
2009/0275984 A1 11/2009 Kim et al.
2010/0004654 A1 1/2010 Schmitz et al.
2010/0049204 A1 2/2010 Soubeiran
2010/0057127 A1 3/2010 McGuire et al.
2010/0094306 A1 4/2010 Chang et al.
2010/0100185 A1 4/2010 Trieu et al.
2010/0106192 A1 4/2010 Barry
2010/0114103 A1 5/2010 Harrison et al.
2010/0114322 A1 5/2010 Clifford et al.
2010/0130941 A1 5/2010 Conlon et al.
2010/0137872 A1 6/2010 Kam et al.
2010/0137911 A1 6/2010 Dant
2010/0145449 A1 6/2010 Makower et al.
2010/0145462 A1 6/2010 Ainsworth et al.
2010/0168751 A1 7/2010 Anderson et al.
2010/0249782 A1 9/2010 Durham
2010/0249847 A1 9/2010 Jung et al.
2010/0256626 A1 10/2010 Muller et al.
2010/0262239 A1 10/2010 Boyden et al.
2010/0280551 A1* 11/2010 Pool .................. A61B 17/7056 606/249
2010/0318129 A1 12/2010 Seme et al.
2010/0331883 A1 12/2010 Schmitz et al.
2011/0004076 A1 1/2011 Janna et al.
2011/0057756 A1 3/2011 Marinescu et al.
2011/0060336 A1* 3/2011 Pool .................. A61B 17/1725 606/62
2011/0066188 A1 3/2011 Seme et al.
2011/0098748 A1 4/2011 Jangra
2011/0118848 A1 5/2011 Giovanni
2011/0152725 A1 6/2011 Demir et al.
2011/0196435 A1 8/2011 Forsell
2011/0202138 A1 8/2011 Shenoy et al.
2011/0238126 A1 9/2011 Soubeiran
2011/0257655 A1 10/2011 Copf, Jr.
2011/0284014 A1 11/2011 Cadeddu et al.
2012/0019341 A1 1/2012 Gabay et al.
2012/0019342 A1 1/2012 Gabay et al.
2012/0053633 A1 3/2012 Stauch
2012/0088953 A1 4/2012 King
2012/0109207 A1 5/2012 Trieu
2012/0116535 A1 5/2012 Ratron et al.
2012/0158061 A1 6/2012 Koch et al.
2012/0172883 A1 7/2012 Sayago
2012/0179215 A1 7/2012 Soubeiran
2012/0203282 A1 8/2012 Sachs et al.
2012/0221106 A1 8/2012 Makower et al.
2012/0271353 A1 10/2012 Barry
2012/0296234 A1 11/2012 Wilhelm et al.
2012/0329882 A1 12/2012 Messersmith et al.
2013/0013066 A1 1/2013 Landry et al.
2013/0072932 A1 3/2013 Stauch
2013/0123847 A1 5/2013 Anderson et al.
2013/0138017 A1 5/2013 Jundt et al.
2013/0138154 A1 5/2013 Reiley
2013/0150863 A1 6/2013 Baumgartner
2013/0150889 A1 6/2013 Fening et al.
2013/0178903 A1 7/2013 Abdou
2013/0211521 A1 8/2013 Shenoy et al.
2013/0245692 A1 9/2013 Hayes et al.
2013/0253344 A1 9/2013 Griswold et al.
2013/0253587 A1 9/2013 Carls et al.
2013/0261672 A1 10/2013 Horvath
2013/0296863 A1 11/2013 Globerman et al.
2013/0296864 A1 11/2013 Burley et al.
2013/0296940 A1 11/2013 Northcutt et al.
2013/0325006 A1 12/2013 Michelinie et al.
2013/0325071 A1 12/2013 Niemiec et al.
2014/0005788 A1 1/2014 Haaja et al.
2014/0025172 A1 1/2014 Lucas et al.
2014/0052134 A1 2/2014 Orisek
2014/0058392 A1 2/2014 Mueckter et al.
2014/0058450 A1 2/2014 Arlet
2014/0066987 A1 3/2014 Hestad et al.
2014/0088715 A1 3/2014 Ciupik
2014/0128920 A1 5/2014 Kantelhardt
2014/0163664 A1 6/2014 Goldsmith
2014/0236234 A1 8/2014 Kroll et al.
2014/0236311 A1 8/2014 Vicatos et al.
2014/0257412 A1 9/2014 Patty et al.
2014/0277446 A1 9/2014 Clifford et al.
2014/0296918 A1 10/2014 Fening et al.
2014/0303538 A1 10/2014 Baym et al.
2014/0303539 A1 10/2014 Baym et al.
2014/0358150 A1 12/2014 Kaufman et al.
2015/0105782 A1 4/2015 D'Lima et al.
2015/0105824 A1 4/2015 Moskowitz et al.

(56) References Cited

U.S. PATENT DOCUMENTS

2015/0272471 A1* 10/2015 Quick ............... A61B 17/7016 600/424
2016/0113683 A1* 4/2016 Cheng ............... A61B 17/8004 606/258

FOREIGN PATENT DOCUMENTS

| | | | |
|---|---|---|---|
| DE | 1541262 | A1 | 6/1969 |
| DE | 8515687 | U1 | 12/1985 |
| DE | 19626230 | A1 | 1/1998 |
| DE | 19745654 | A1 | 4/1999 |
| DE | 102005045070 | A1 | 4/2007 |
| EP | 0663184 | A1 | 7/1995 |
| EP | 1905388 | A1 | 4/2008 |
| FR | 2901991 | A1 | 12/2007 |
| FR | 2900563 | B1 | 8/2008 |
| FR | 2892617 | B1 | 9/2008 |
| FR | 2916622 | B1 | 9/2009 |
| FR | 2961386 | B1 | 12/2011 |
| JP | H0956736 | | 3/1997 |
| JP | 2002500063 | A | 1/2002 |
| WO | WO1998044858 | A1 | 10/1998 |
| WO | WO1999051160 | A1 | 10/1999 |
| WO | WO2001024697 | A1 | 4/2001 |
| WO | WO2001045485 | A3 | 6/2001 |
| WO | WO2001045487 | A2 | 6/2001 |
| WO | WO2001067973 | A2 | 9/2001 |
| WO | WO2001078614 | A1 | 10/2001 |
| WO | WO2006090380 | | 8/2006 |
| WO | WO2007013059 | A3 | 2/2007 |
| WO | WO2007015239 | | 2/2007 |
| WO | WO2007015239 | A3 | 2/2007 |
| WO | WO2007118179 | | 10/2007 |
| WO | WO2011116158 | A3 | 9/2011 |
| WO | WO2013119528 | A1 | 8/2013 |
| WO | WO2014040013 | A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™M System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening. ", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", SPINE, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

(56) References Cited

OTHER PUBLICATIONS

Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", SPINE, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.

(56) References Cited

OTHER PUBLICATIONS

Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", SPINE, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.
Gebhart, M. Neel M., Soubeiran A., Dubouseet, J., "Early clinical experience with a custom made growing endoprosthesis in children with malignant bone tumors of the lower etremity actioned by an external permanent magnet: the Phenix M. system", International society of Limb Salvage 14th International Symposium on Limb Salvage, Sep. 13, 2007, Hamburg German.
Gupta, A., Meswnia, J., Pollock, R., Cannon, S., Briggs, T., Taylor, S., Blunn, G., "Non-Invasive Distal Femoral Expandable Endoprosthesis for Limb-Salvage Surgery in Paediatric Tumours", The Journal of Bone and Joint Surgery British Edition, 2006, vol. 88-B, No. 5, pp. 649-654, Churchill Livingstone, London, England.
Soubeiran, A. Gebhart, M., Miladi, L., Griffet, J., Neel, M., Dubousset, J., "the Phenix M System, a fully implanted non-invasive lengthening device externally controllable through the skin with a palm size permanent magnent. Applications in limb salvage." International Society of Limb Salvage 14th International Symposium on Limb Salvage, Sep. 13, 2007 Hamburg, Germany.
Verkerke, G., Koops, H., Veth, R., Oldhoff, J., Nielsen, H., vanden Kroonenberg, H., Grottenboer, H., van Krieken, F., "Design of a Lengthening Element for a Modular Femur Endoprosthetic System", Proceedings of the Institution of Mechanical Engineers Part H: Journal of Engineering in Medicine, 1989, vol. 203, No. 2, pp. 97-102, Mechanical Engineering Publications, London, England.
Verkerke, G., Koos, H., Veth R., van den Kroonenberg, H., Grottenboer, H., Nielsen, H., Oldhoff, J., Postma, A., "An Extendable Modular Endoprosthetic System for Bone Tumor Management in the Leg", Journal of Biomedical Engineering, 1990, vol. 12, No. 2, pp. 91-96. Butterfield Scientific Limited, Guilford, England.
Micromotion "Micro Drive Engineering-General catalogue" pp. 14-24; Jun. 2009.

* cited by examiner 10
12
14
16
18
20
22
24
26
28
30
32
34
36
38
40
42
A
B
C
C'

INTERSPINOUS PROCESS DEVICE AND METHOD

CROSS REFERENCE TO RELATED APPLICATIONS

This application is a continuation of U.S. patent application Ser. No. 16/597,702, filed Oct. 9, 2019, which is a continuation of U.S. patent application Ser. No. 15/454,899, filed Mar. 9, 2017, now U.S. Pat. No. 10,478,232, which is a continuation of U.S. patent application Ser. No. 12/761,141, filed Apr. 15, 2010, now U.S. Pat. No. 9,622,792, which claims the benefit of U.S. provisional application No. 61/173,902, which was filed on Apr. 29, 2009, each of which is incorporated by reference in its entirely herein.

FIELD

The field of the invention generally relates to medical devices for treating disorders of the skeletal system and in particular the spinal system.

BACKGROUND

As individuals age, their spinal discs tend to degenerate over time. This can result in a decrease in the disc space height. In addition, the facets and ligaments of the spine degenerate as well over time. These problems can lead to a reduction in the foramenal height of the vertebrae. The foramen is a natural opening between the vertebrae that allows the passage of respective nerves from the spinal cord. Because the nerves pass through the respective foramen, a reduction in the foramenal height may often cause nerve tissue to get pinched leading to various types of back pain. These pinched or compressed nerves can also lead to difficulty in walking.

Surgical solutions to this problem require the surgical removal of the ligaments and bone that are causing the compression. A number of interspinous process devices have been designed to act as spacers to flex the spine and open the canal, lateral recess and foramen to take pressure off of the compressed or pinched nerves. Designs vary from static spacers to dynamic, spring-like devices. These may be made from bone allograft, titanium, polyether ether ketone (PEEK), and elastomeric compounds. The common goal between these devices is to mechanically distract the spinous processes and blocking extension (of the abdominal muscles) that affect the intervertebral relationship. Examples of these include the X STOP device (Medtronic, Memphis, TN), ExtenSure device (NuVasive, San Diego, CA), and the Wallis system (Abbott Spine, Bordeaux, France). Often, these devices are successful in alleviating symptoms of patients post surgery, however, many patients have recurring symptoms after months or years have passed.

SUMMARY

The invention is an interspinous process device that is capable of providing distraction at multiple times after the initial surgery without requiring additional surgeries. In the first embodiment of the invention, an interspinous process device is configured for placement between adjacent spinous processes on a subject's spine. The device includes a housing configured for mounting to a first spinal process, the housing having a lead screw fixedly secured at one end thereof. A magnetic assembly is at least partially disposed within the housing and configured for mounting to a second spinal process. The magnetic assembly includes a hollow magnet configured for rotation within the magnetic assembly, the hollow magnet comprising a threaded insert configured to engage with the lead screw. An externally applied magnetic field rotates the hollow magnet in a first direction or a second, opposite direction. Rotation of the hollow magnet in the first direction causes telescopic movement of the magnetic assembly out of the housing (i.e., elongation) and rotation in the second direction causes telescopic movement of the magnetic assembly into the housing (i.e., shortening).

In a second aspect of the invention, a method of adjusting the distance between adjacent spinous processes in a subject includes affixing an interspinous process device to first and second spinous processes. The interspinous process device including a housing configured for mounting to the first spinal process, the housing comprising a lead screw fixedly secured at one end thereof. The interspinous device further includes a magnetic assembly at least partially disposed within the housing and configured for mounting to the second spinal process, the magnetic assembly comprising a hollow magnet configured for rotation within the magnetic assembly. The hollow magnet includes a threaded insert configured to engage with the lead screw. An external magnetic field is applied non-invasively to rotate the hollow magnet, wherein rotation of the hollow magnet in a first direction increases the distance between adjacent spinous processes and rotation of the hollow magnet in the second direction decreases the distance between adjacent spinous processes.

BRIEF DESCRIPTION OF THE DRAWINGS

FIG. 7A illustrates the hollow magnet in the 0° position.

FIG. 7B illustrates the hollow magnet in the 90° position.

FIG. 7C illustrates the hollow magnet in the 180° position.

FIG. 7D illustrates the hollow magnet in the 270° position.

DETAILED DESCRIPTION

Figures 1A, 1B, 1C:
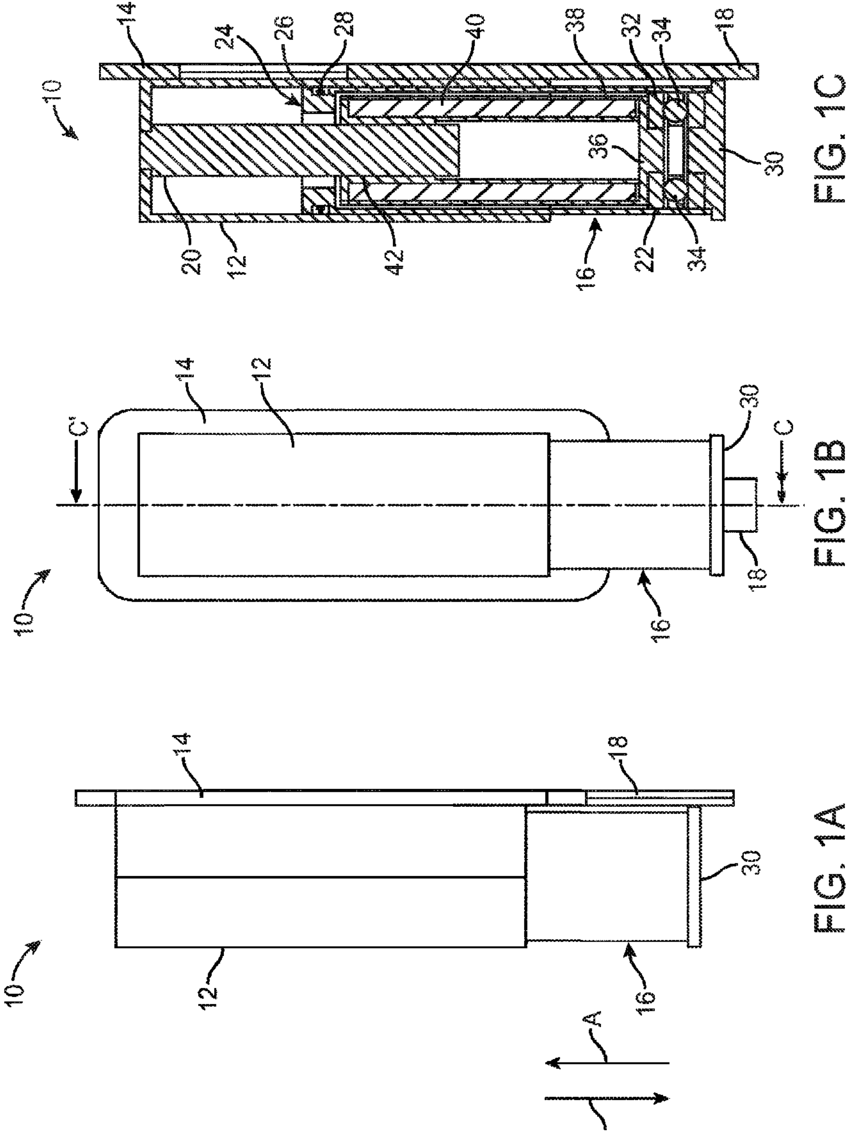
FIG. 1A illustrates side view of an interspinous process device according to one embodiment.
FIG. 1B illustrates a top plan view of the interspinous process device of FIG. 1A.
FIG. 1C illustrates a cross-sectional view of the interspinous process device of FIGS. 1A and 1B taken along the line C-C' of FIG. 1B.
Figure 3:
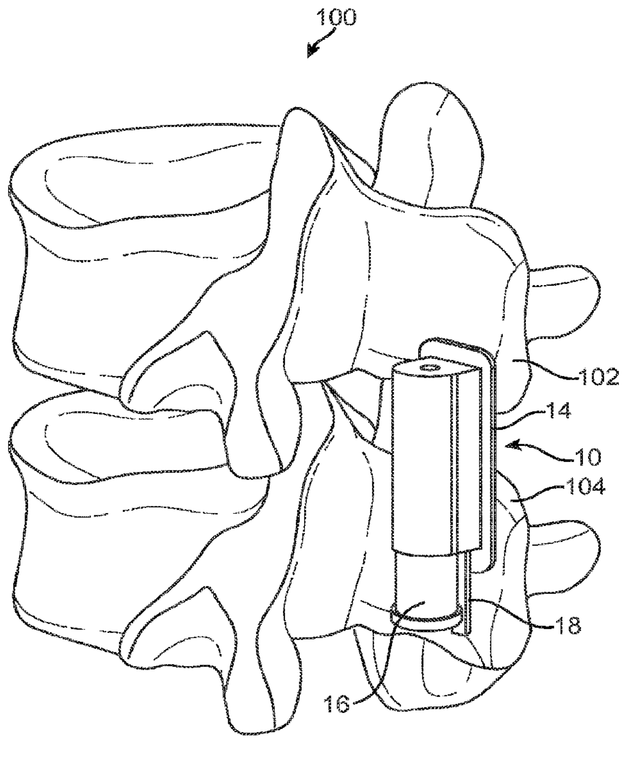
FIG. 3 illustrates an interspinous process device secured to adjacent spinous processes on a subject's spine.

FIGS. 1A, 1B, and 1C illustrate an interspinous process device 10 according to one embodiment. The interspinous process device 10 is configured to mount on a subject's spine 100 as illustrated in FIG. 3. For example, the interspinous process device 10 is mounted between adjacent spinous processes 102, 104. The interspinous process device 10 is configured to adjust its length in a non-invasive manner. As explained herein in more detail, an external adjustment device 1130 (FIGS. 4, 5, 6, 7A-7D, and 8) is provided that can lengthen or shorten the interspinous process device 10 on an as needed basis. The interspinous process device 10 includes a housing 12 that is affixed or otherwise coupled to a first mounting surface 14. The housing 12 may be made of any biocompatible, non-magnetic material such as, for instance, stainless steel, titanium, or the like. A moveable magnetic assembly 16 is telescopically disposed within the housing 12. The magnetic assembly 16 is moveable in the direction of arrows A and B of FIG. 1A. The magnetic assembly 16 is affixed or otherwise coupled to a second mounting surface 18. The second mounting surface 18 is moveable with respect to the first mounting surface 14. In this regard, as the magnetic assembly 16 is advanced out of the housing 12, a distraction force is applied to the adjacent spinous processes 102, 104 (FIG. 3). This distraction force can be increased by advancing the device an additional amount. Conversely, as the magnetic assembly 16 is advanced into the housing 12, a compressive force (or relaxing as the case may be, for example, a decreased distraction force) is applied to the adjacent spinous processes 102, 104.

FIGS. 1A and 1B illustrate side and plan views, respectively, of the interspinous process device 10. FIG. 1C illustrates a cross-sectional view of the interspinous process device 10 taken along the line C-C' of FIG. 1B. As best seen in FIG. 1C, a lead screw 20 is fixedly secured at one end to the housing 12. The lead screw 20 has threads having, preferably, a very fine pitch, for example, 80 to 100 threads per inch, in order to minimize friction between the lead screw 20 and the a threaded insert (described in more detail below), and thus, minimize the required torque. The materials of the lead screw 20 may be made from non-magnetic, implantable materials such as titanium, though they may also be made from other magnetic materials such as stainless steel. Additionally, lubrication may be added to the lead screw and/or threaded insert to further minimize friction. For example, biocompatible silicone or Krytox© (perfluorinated polyether-based oil available from DuPont) may be added.

Turning now to the magnetic assembly 16, which is best illustrated in FIG. 1C, the magnetic assembly 16 itself includes a housing 22 that terminates at one end at an O-ring gland 24. The O-ring gland 24 includes a recess 26 dimensioned to receive an O-ring 28 that is compressed between an inner surface of the housing 12 and the recess 26. The O-ring 28 thus provides a dynamic sealing surface as the magnetic assembly 16 moves into and out of the housing 12. The opposing end of the magnetic assembly 16 includes an end cap 30 that effectively seals the interior of the magnetic assembly 16 from the external environment. End cap 30 is joined with housing 12 by various methods, for example laser or E-beam welding. Adjacent to the end cap 30 is a thrust bearing 32 that includes a plurality of ball bearings 34 and a central aperture (not shown) dimensioned to receive an axle 36 of a retaining cup 38. The retaining cup 38 is thus rotationally mounted with respect to the thrust bearing 32. The retaining cup 38 may be made of stainless steel or a non-magnetic material such as titanium.

Still referring to FIG. 1C, a hollow magnet 40 is mounted inside the retaining cup 38. The hollow magnet 40 may include, for example, a permanent magnet. The hollow magnet 40 may be formed from a rare earth magnet, preferably Neodymium-Iron-Boron. Other magnetic materials may be used, including SmCo (Samarium Cobalt), which is typically available as SmCo5, or SmCo15, Sm2Co17, or AlNiCo (Aluminum Nickel Cobalt). In still other embodiments, Iron Platinum (Fe—Pt) may be used. The hollow magnet 40 may be bonded to the interior of the retaining cup 38 using, for example, an adhesive or epoxy. A threaded insert 42 having a female thread is located in the hollow portion of the magnet 40. FIG. 1C illustrates the threaded insert 42 that is located at one end of the hollow magnet 40. The threaded insert 42 is bonded or otherwise affixed to an inner surface of the hollow magnet 40 so that when the hollow magnet 40 rotates, the threaded insert 42 rotates in unison.

Figure 2:
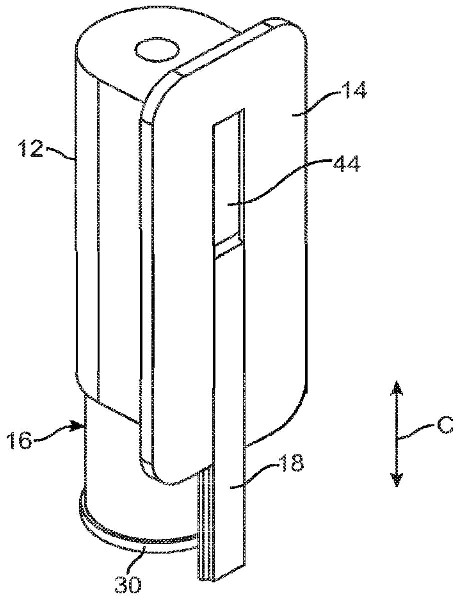
FIG. 2 illustrates a perspective view of the interspinous process device.

As explained in more detail below, an external magnetic field is applied to the subject having the implanted interspinous process device 10. The interspinous process device 10 can then be lengthened or shortened to increase or decrease the foramenal height of the vertebrae. FIG. 2 illustrates a perspective view of the interspinous process device 10 with the first and second mounting surfaces 14, 18 exposed for better viewing. As seen in FIG. 2, a channel 44 is provided in the first mounting surface 14 and is dimensioned to receive the second mounting surface 18. The channel 44 may be milled or otherwise formed with a step or other geometry that enables the second mounting surface 18 to slide back and forth in the direction of arrow C. A low friction coating may be applied to the channel 44 and/or the interface with the second mounting surface 18 to reduce frictional forces. The first and second mounting surfaces 14, 18 may be affixed to the adjacent spinous processes 102, 104 using any number of affixation techniques known to those skilled in the art. These include, for example, screws, hooks, clamps, and the like. FIG. 3 illustrates an interspinous process device 10 mounted between adjacent spinous processes 102, 104. In this view, the actual affixation mechanism is omitted to better illustrate the relationship between the interspinous process device 10 and the spinous processes 102, 104.

Figure 9:
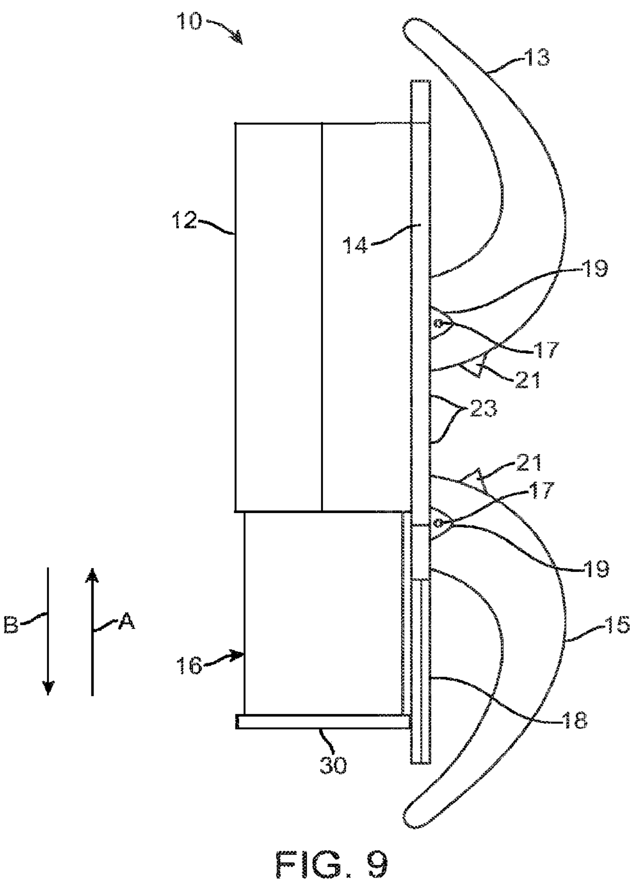
FIG. 9 illustrates side view of an interspinous process device according to another embodiment. Hooks are illustrated in a low-profile configuration.
Figure 10:
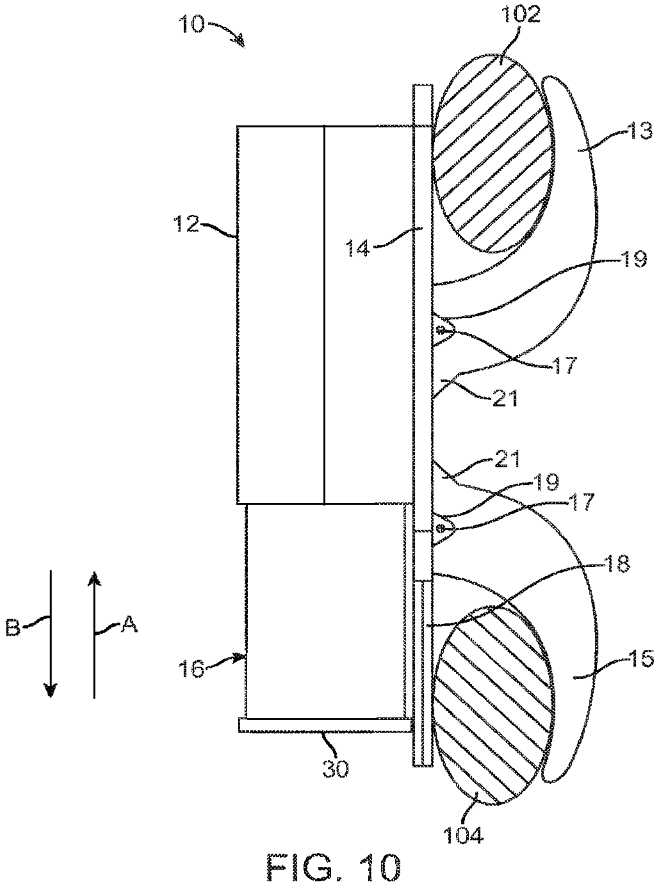
FIG. 10 illustrates side view of an interspinous process device according to another embodiment. Hooks are illustrated in a deployed configuration.

FIGS. 9 and 10 show an embodiment having two upward facing hooks 13 (one hook obscured from view) coupled to the two sides of the first mounting surface 14 and one downward facing hook 15 coupled to the second mounting surface 18. Upward facing hooks 13 are configured for cradling the lower portion of spinous process 102, and downward facing hook 15 is configured for cradling the upper portion of spinous process 104, allowing the positive displacement of the interspinous process device 10 to distract between the spinous processes 102, 104. Hooks 13, 15 may additionally be configured to be able to fold, retract, or pivot out of the way during insertion to allow for a less invasive insertion (e.g., a smaller incision results in less trauma). Hooks 13, 15 are attached to interspinous process device 10 with axles 17 extending between pairs of mounts 19. The axles 17 extend through holes (not shown) in hooks 13, 15. FIG. 9 shows the embodiment with the hooks 13, 15 folded or pivoted out of the way for a lower profile, and FIG. 10 shows the hooks 13, 15 in position to distract spinous processes 102, 104. Stops 21 are configured to abut flat surface 23 so that hooks 13, 15 are held static in the configuration of FIG. 10.

Figure 4:
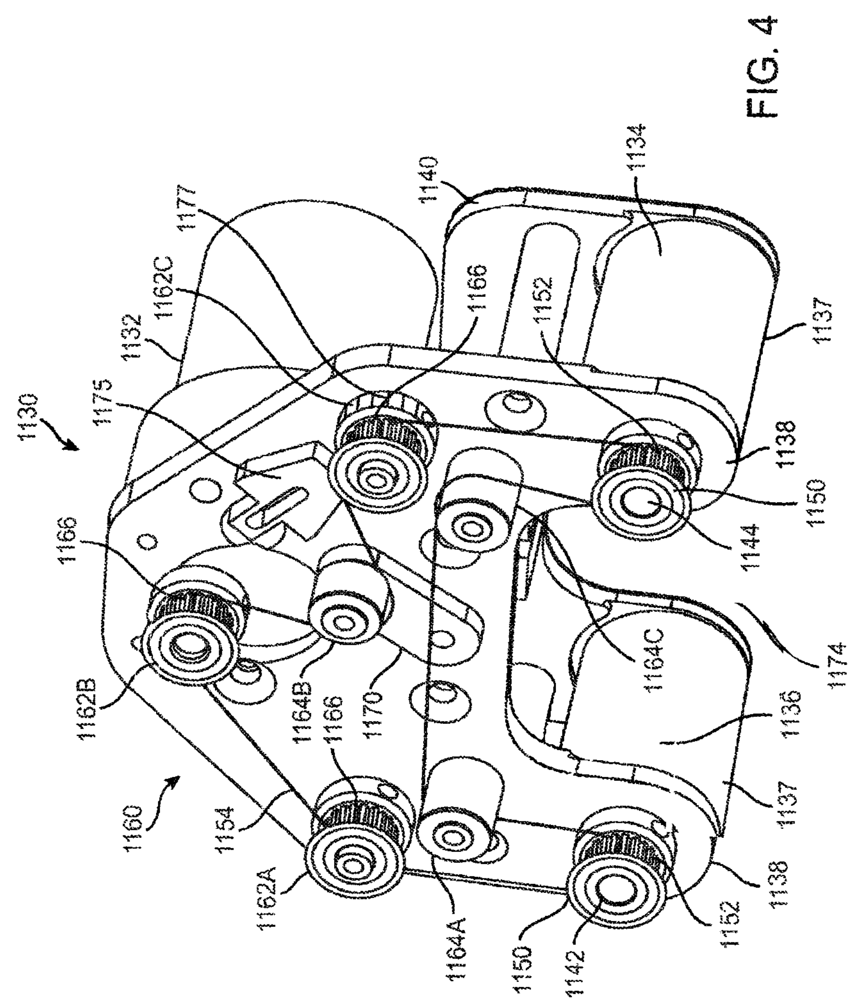
FIG. 4 illustrates a perspective view of an external adjustment device according to one embodiment. The outer housing or cover is removed to illustrate the various aspects of the external adjustment device.

FIG. 4 illustrates an external adjustment device 1130 that may be used to externally impart rotational motion or "drive" the magnetic assembly 16. The external adjustment device 1130 includes a motor 1132 that is used to impart rotational movement to two permanent magnets 1134, 1136. The two permanent magnets 1134, 1136 are located in the same driver 1130 and are configured for placement on the same side of the body of the patient or subject. The motor 1132 may include, for example, a DC powered motor or servo that is powered via one or more batteries (not shown) integrally contained within the external adjustment device 1130. Alternatively, the motor 1132 may be powered via a power cord or the like to an external power source. For example, the external power source may include one or more batteries or even an alternating current source that is converted to DC.

Still referring to FIG. 4, the two permanent magnets 1134, 1136 are preferably cylindrically-shaped permanent magnets. The permanent magnets may be made from, for example, a rare earth magnet material such as Neodymium-Iron-Boron (NdFeB) although other rare earth magnets are also possible. For example, each magnet 1134, 1136 may have a length of around 1.5 inches and a diameter of around 1.0 to 3.5 inches. Both magnets 1134, 1136 are diametrically magnetized (poles are perpendicular the longitudinal axis of each permanent magnet 1134, 1136). The magnets 1134, 1136 may be contained within a non-magnetic cover or housing 1137. In this regard, the magnets 1134, 1136 are able to rotate within the stationary housing 1137 that separates the magnets 1134, 1136 from the external environment. Preferably, the housing 1137 is rigid and relatively thin walled at least at the portion directly covering the permanent magnets 1134, 1136, in order to minimize the gap between the permanent magnets 1134, 1136 and the magnetic assembly 16 (not shown in FIGS. 7A-7D for clarity purposes).

As seen in FIG. 4, the permanent magnets 1134, 1136 are rotationally mounted between opposing base members 1138, 1140. Each magnet 1134, 1136 may include axles or spindles 1142, 1144 mounted on opposing axial faces of each magnet 1134, 1136. The axles 1142, 1144 may be mounted in respective bearings (not shown) that are mounted in the base members 1138, 1140. As seen in FIG. 4, driven pulleys 1150 are mounted on one set of axles 1142 and 1144. The driven pulleys 1150 may optionally include grooves or teeth 1152 that are used to engage with corresponding grooves or teeth 1156 (partially illustrated in FIG. 5) contained within a drive belt (indicated by path 1154) or drive chain.

Figure 6:
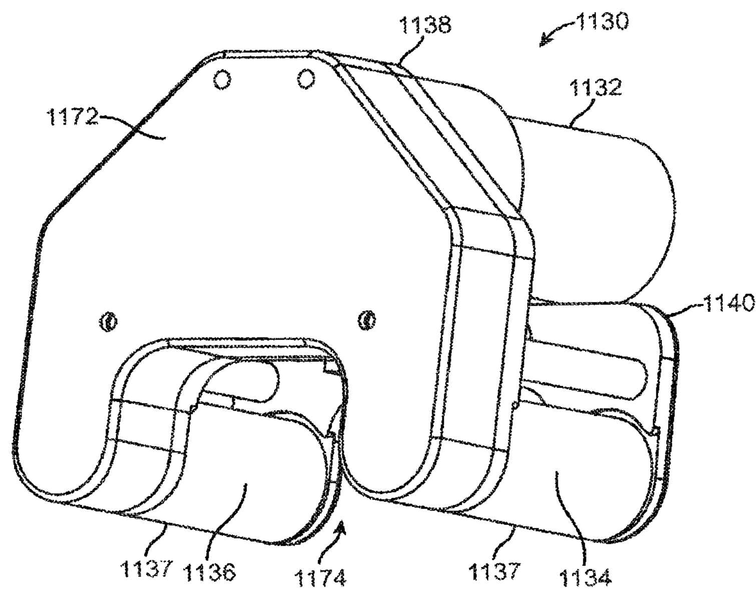
FIG. 6 illustrates a perspective view of an external adjustment device of FIG. 4 with the outer housing or cover in place.

Still referring to FIG. 4, the external adjustment device 1130 includes a drive transmission 1160 that includes the two driven pulleys 1150 along with a plurality of pulleys 1162A, 1162B, 1162C and rollers 1164A, 1164B, 1164C on which the drive belt 1154 is mounted. The pulleys 1162A, 1162B, 1162C may optionally include grooves or teeth 1166 used for gripping corresponding grooves or teeth 1156 of the drive belt 1154 or drive chain. Pulleys 1162A, 1162B, 1162C and rollers 1164A, 1164B, 1164C may be mounted on respective bearings (not shown). As seen in FIG. 4, pulley 1162B is mechanically coupled to the drive shaft (not shown) of the motor 1132. The pulley 1162B may be mounted directly to the drive shaft or, alternatively, may be coupled through appropriate gearing. One roller 1164B is mounted on a biased arm 1170 and thus provides tension to the belt 1154. The various pulleys 1150, 1162A, 1162B, 1162C and rollers 1164A, 1164B, 1164C along with the drive belt 1154 may be contained within a cover or housing 1172 that is mounted to the base 1138 (as seen in FIG. 6). For safety and convenience, it may be desired for the external adjustment device 1130 to have a removable safety cover that would be placed over the portion containing the permanent magnets 1134, 1136, for example during storage, so that the high magnetic field cannot come closely in contact with anything that would be strongly attracted to it or damaged by it. The external adjustment device 1130 may also be supplied in a case, for example, a case that has a sheet made of a magnetic shielding material, to minimize the magnetic field external to the case. Giron or mu-metal are two examples of this material.

Figure 5:
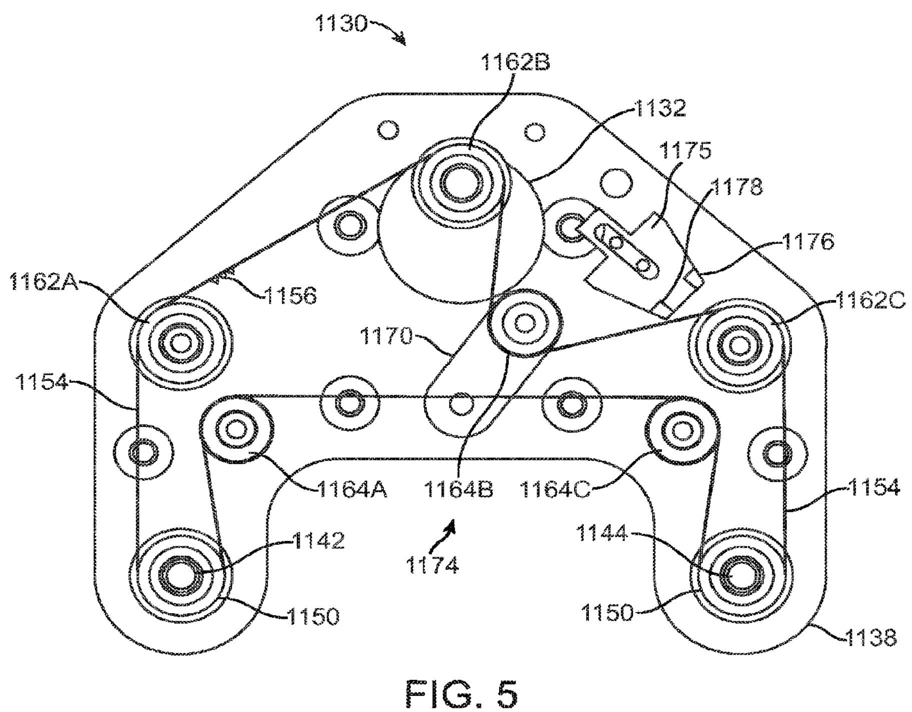
FIG. 5 illustrates a side or end view of the external adjustment device of FIG. 4.
Figures 7A, 7B:
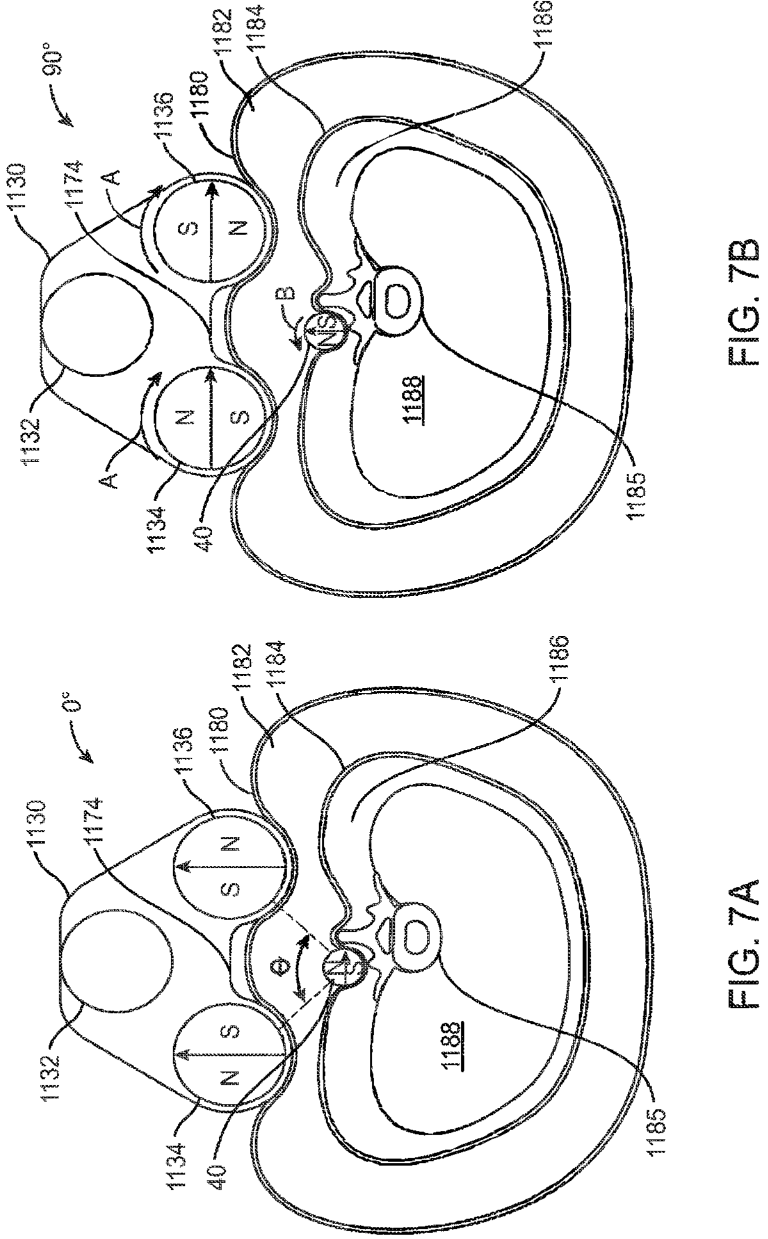
FIG. 7A illustrates a cross-sectional representation of the external adjustment device being positioned on a patient's skin.
FIG. 7B illustrates a cross-sectional representation of the external adjustment device being positioned on a patient's skin.

As seen in FIGS. 4 and 5, rotational movement of the pulley 1162B causes the drive belt 1154 to move around the various pulleys 1150, 1162A, 1162B, 1162C and rollers 1164A, 1164B, 1164C. In this regard, rotational movement of the motor 1132 is translated into rotational movement of the two permanent magnets 1134, 1136 via the drive transmission 1160. In one aspect of the invention, the base members 1138, 1140 are cut so as to form a recess 1174 that is located between the two magnets 1134, 1136. During use, the external adjustment device 1130 is pressed against the skin of a patient, or against the clothing which covers the skin (e.g., the external adjustment device 1130 may be used through clothing so the patient may not need to undress). A small permanent magnet may be temporarily placed on the patient's clothing to determine the location of the hollow magnet 40 (via the attraction of the two magnets). The recess 1174 allows skin as well as the underlying tissue to gather or compress within the recessed region 1174 as seen in FIGS. 7A and 7B. This advantageously reduces the overall distance between the external drive magnets 1134, 1136 and the hollow magnet 40 contained within the magnetic assembly 16. By reducing the distance, this means that the externally located magnets 1134, 1136 and/or the hollow magnet 40 may be made smaller. This reduction in distance is especially useful in the case of an obese patient.

In one embodiment, the two permanent magnets 1134, 1136 are configured to rotate at the same angular velocity. In another embodiment, the two permanent magnets 1134, 1136 each have at least one north pole and at least one south pole, and the external adjustment device 1130 is configured to rotate the first magnet 1134 and the second magnet 1136 such that the angular location of the at least one north pole of the first magnet 1134 is substantially equal to the angular location of the at least one south pole of the second magnet 1136 through a full rotation of the first and second magnets 1134, 1136.

FIGS. 7A and 7B illustrate cross-sectional views of the patient having an implanted magnetic assembly (not shown for sake of clarity) with a hollow magnet 40. The hollow magnet 40 is seen disposed on one side of a vertebra 1185 although the hollow magnet 40 may be located elsewhere depending on the particular affixation point on the spinous processes. FIGS. 7A and 7B illustrate an obese patient in which skin and other tissue gather within the recess 1174. As seen in FIGS. 7A and 7B the excess skin and other tissue are easily accommodated within the recess 1174 to enable close positioning between the hollow magnet 40 and the external drive magnets 1134, 1136. For many patients, the air gap or distance between the hollow magnet 40 and the external drive magnets 1134, 1136 is generally one inch or less. In FIGS. 7A through 7D, the hollow magnet 40 is depicted somewhat larger than its actual size in order for its respective poles to be more clearly visible.

Still referring to FIGS. 4 and 5, the external adjustment device 1130 preferably includes an encoder 1175 that is used to accurately and precisely measure the degree of movement (e.g., rotational) of the external magnets 1134, 1136. In one embodiment, an encoder 1175 is mounted on the base member 1138 and includes a light source 1176 and a light receiver 1178. The light source 1176 may include a LED which is pointed or directed toward pulley 1162C. Similarly, the light receiver 1178 may be directed toward the pulley 1162C. The pulley 1162C includes a number of reflective markers 1177 regularly spaced about the periphery of the pulley 1162C. Depending on the rotational orientation of the pulley 1162C, light is either reflected or not reflected back onto the light receiver 1178. The digital on/off signal generated by the light receiver 1178 can then be used to determine the rotational speed and displacement of the external magnets 1134, 1136.

FIGS. 7A, 7B, 7C, and 7D illustrate the progression of the external magnets 1134, 1136 and the hollow magnet 40 that is located within the magnetic assembly 16 during use. FIGS. 7A, 7B, 7C, and 7D illustrate the external adjustment device 1130 being disposed against the external surface of the patient's skin 1180 adjacent the spine. In the non-invasive adjustment procedure depicted, the patient 100 lies in a prone position, and the external adjustment device 1130 is placed upon the patient's back. However, the adjustment is conceived possible with the patient in supine, standing or other positions. The external adjustment device 1130 is placed against the skin 1180 in this manner to remotely rotate the hollow magnet 40. As explained herein, rotation of the hollow magnet 40 causes rotational movement of the threaded insert 42. This rotational movement is then translated to the lead screw 20. Depending on the rotational direction of the lead screw 20, the magnetic assembly 16 moves in a telescopic manner out of or into the housing 12. In this regard, by controlling the rotational movement of the hollow magnet 40 using the external adjustment device 1130, the operator is able to adjust the linear displacement of the interspinous process device 10 in a controllable manner. The hollow magnet 40 may have rotational movement though less than 360° of a full rotation. Alternatively, the hollow magnet 40 may have rotational movement through more than 360° (e.g., multiple, full revolutions).

As seen in FIGS. 7A, 7B, 7C, and 7D, the external adjustment device 1130 may be pressed down on the patient's skin 1180 with some degree of force such that skin 1180 and other tissue such as the underlying layer of fat 1182 are pressed or forced into the recess 1174 of the external adjustment device 1130. FIGS. 7A, 7B, 7C, and 7D show the magnetic orientation of the hollow magnet 40 as it undergoes a full rotation in response to movement of the permanent magnets 1134, 1136 of the external adjustment device 1130.

With reference to FIG. 7A, the hollow magnet 40 is shown being oriented with respect to the two permanent magnets 1134, 1136 via an angle θ. This angle θ may depend on a number of factors including, for instance, the separation distance between the two permanent magnets 1134, 1136, the location or depth of where the hollow magnet 40 is located, the degree of force at which the external adjustment device 1130 is pushed against the patient's skin. Generally in applications including some obese patients, the angle θ should be at or around 90° to achieve maximum drivability (e.g., torque). An angle of about 70° is preferred for the majority of patients when the permanent magnets 1134, 1136 have an outer diameter of about two (2.0) to three (3.0) inches.

FIG. 7A illustrates the initial position of the two permanent magnets 1134, 1136 and the hollow magnet 40. This represents the initial or starting location (e.g., 0° position as indicated). Of course, it should be understood that, during actual use, the particular orientation of the two permanent magnets 1134, 1136 and the hollow magnet 40 will vary and not likely will have the starting orientation as illustrated in FIG. 7A. In the starting location illustrated in FIG. 7A, the two permanent magnets 1134, 1136 are oriented with their poles in an N-S/S-N arrangement. The hollow magnet 40 is, however, oriented generally perpendicular to the poles of the two permanent magnets 1134, 1136.

Figures 7C, 7D:
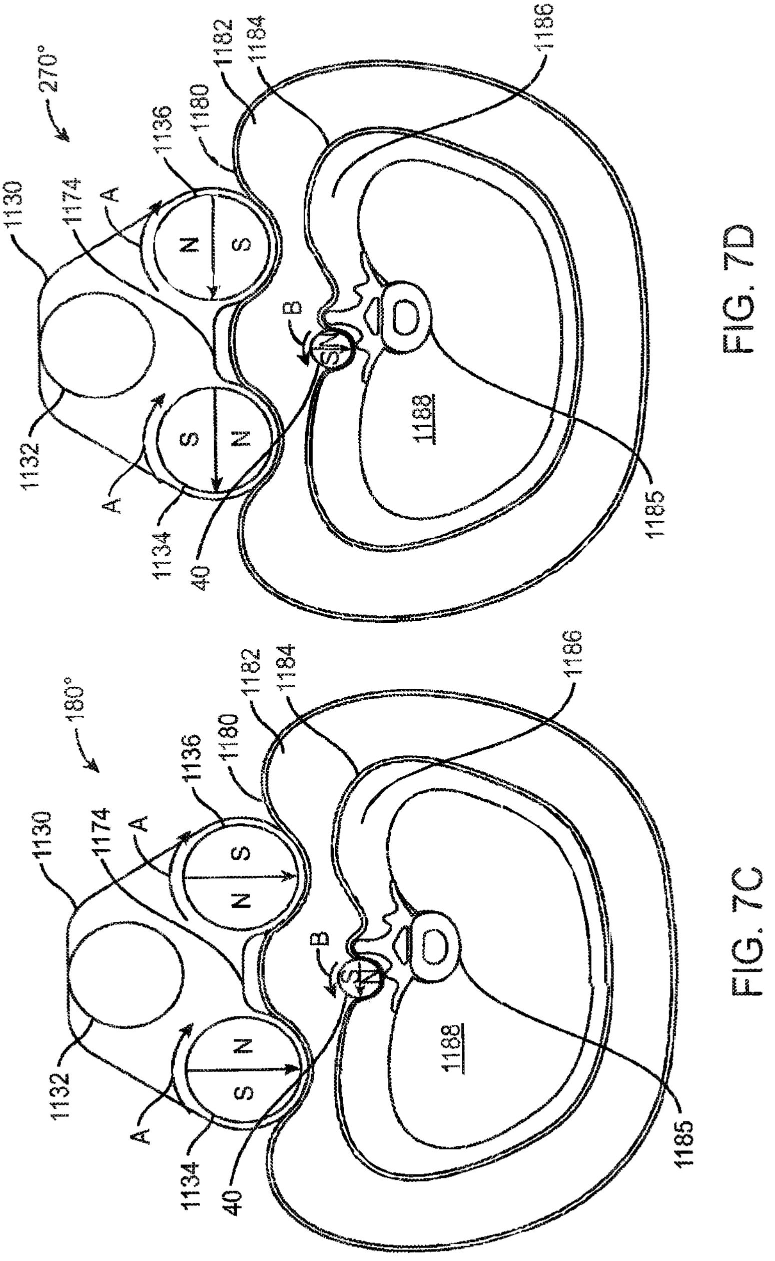
FIG. 7C illustrates a cross-sectional representation of the external adjustment device being positioned on a patient's skin.
FIG. 7D illustrates a cross-sectional representation of the external adjustment device being positioned on a patient's skin.

FIG. 7B illustrates the orientation of the two permanent magnets 1134, 1136 and the hollow magnet 40 after the two permanent magnets 1134, 1136 have rotated through 90°. The two permanent magnets 1134, 1136 rotate in the direction of arrow A (e.g., clockwise) while the hollow magnet 40 rotates in the opposite direction (e.g., counter clockwise) represented by arrow B. It should be understood that the two permanent magnets 1134, 1136 may rotate in the counter clockwise direction while the hollow magnet 40 may rotate in the clockwise direction. Rotation of the two permanent magnets 1134, 1136 and the hollow magnet 40 continues as represented by the 180° and 270° orientations as illustrated in FIGS. 7C and 7D. Rotation continues until the starting position (0°) is reached again.

During operation of the external adjustment device 1130, the permanent magnets 1134, 1136 may be driven to rotate the hollow magnet 40 through one or more full rotations in either direction to increase or decrease the foramenal distance between spinous processes 102, 104. Of course, the permanent magnets 1134, 1136 may be driven to rotate the hollow magnet 40 through a partial rotation as well (e.g., ¼, ⅛, 1/16, etc.). The use of two magnets 1134, 1136 is preferred over a single external magnet because the hollow magnet 40 may not be oriented perfectly at the start of rotation, so one external magnet 1134, 1136 may not be able to deliver its maximum torque, which depends on the orientation of the hollow magnet 40 some degree. However, when two (2) external magnets (1134, 1136) are used, one of the two 1134 or 1136 will have an orientation relative to the hollow magnet 40 that is better or more optimal than the other. In addition, the torques imparted by each external magnet 1134, 1136 are additive. In prior art magnetically driven devices for other medical applications, the external driving device is at the mercy of the particular orientation of the internal driven magnet. The two-magnet embodiment described herein is able to guarantee a larger driving torque—as much as 75% more than a one-magnet embodiment in the spinal application—and thus the hollow magnet 40 can be designed smaller in dimension, and less massive. A smaller hollow magnet 40 will have a smaller image artifact when performing MRI (Magnetic Resonance Imaging), especially important when using pulse sequences such as gradient echo, which is commonly used in breast imaging, and leads to the largest artifact from implanted magnets. In certain configurations, it may even be optimal to use three or more external magnets, including one or more magnets each on two different sides of the body (for example front and back).

Figure 8:
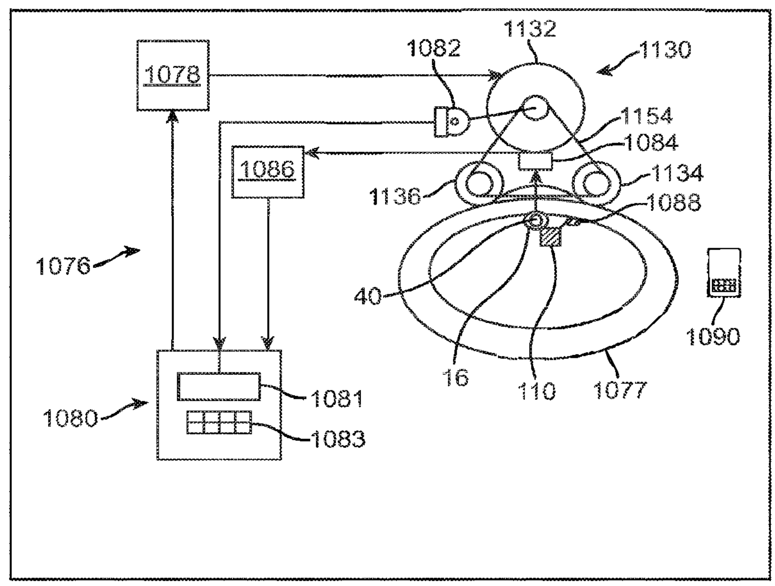
FIG. 8 schematically illustrates a system for driving the external adjustment device according to one embodiment.

FIG. 8 illustrates a system 1076 according to one aspect of the invention for driving the external adjustment device 1130. FIG. 8 illustrates the external adjustment device 1130 pressed against the surface of a patient 1077 (torso face down shown in cross-section). The portion of the magnetic assembly 16 containing the hollow magnet 40 is illustrated. The hollow magnet 40 that is located within the magnetic assembly 16 (disposed internally within the patient 1077 is magnetically coupled through the patient's skin and other tissue to the two external magnets 1134, 1136 located in the external adjustment device 1130. As explained herein, one rotation of the external magnets 1134, 1136 causes a corresponding single rotation of the hollow magnet 40. Turning hollow magnet 40 in one direction causes the interspinous process device 10 to lengthen, or increase distraction force while turning in the opposite direction causes the interspinous process device 10 to shorten, or decrease distraction force. Changes to the interspinous process device 10 are directly related to the number of turns of the hollow magnet 40. In an alternative embodiment, a ratchet may be added which allows motion in one direction, but not the other. For example, the device could be made to be extendable, but not retractable.

The motor 1132 of the external adjustment device 1130 is controlled via a motor control circuit 1078 operatively connected to a programmable logic controller (PLC) 1080. The PLC 1080 outputs an analog signal to the motor control circuit 1078 that is proportional to the desired speed of the motor 1132. The PLC 1080 may also select the rotational direction of the motor 1132 (i.e., forward or reverse). In one aspect, the PLC 1080 receives an input signal from a shaft encoder 1082 that is used to identify with high precision and accuracy the exact relative position of the external magnets 1134, 1136. For example, the shaft encoder 1082 may be an encoder 1175 as described in FIGS. 4-5. In one embodiment, the signal is a pulsed, two channel quadrature signal that represents the angular position of the external magnets 1134, 1136. The PLC 1080 may include a built in screen or display 1081 that can display messages, warnings, and the like. The PLC 1080 may optionally include a keyboard 1083 or other input device for entering data. The PLC 1080 may be incorporated directly into the external adjustment device 1130 or it may be a separate component that is electrically connected to the main external adjustment device 1130.

In one aspect of the invention, a sensor 1084 is incorporated into the external adjustment device 1130 that is able to sense or determine the rotational or angular position of the hollow magnet 40. The sensor 1084 may acquire positional information using, for example, sound waves, ultrasonic waves, radiation (e.g., light), or even changes or perturbations in the magnetic or electromagnetic field between the hollow magnet 40 and the external magnets 1134, 1136. For example, the sensor 1084 may detect photons or light that is reflected from the hollow magnet 40 or a coupled structure (e.g., rotor) that is attached thereto. For example, light may be passed through the patient's skin and other tissue at wavelength(s) conducive for passage through tissue. Portions of the hollow magnet 40 or associated structure may include a reflective surface that reflects light back outside the patient as the hollow magnet 40 (for instance the magnetic assembly 16 may transmit light at least partially there through). The reflected light can then be detected by the sensor 1084 which may include, for example, a photodetector or the like.

In another aspect, the sensor 1084 may operate on the Hall effect, wherein two additional magnets are located within the interspinous process device 10. The additional magnets move axially in relation to each other as the hollow magnet 40 rotates and therefore as the distraction increases or decreases, allowing the determination of the current size of the interspinous process device 10. In yet another aspect, the sensor 1084 may be a strain gauge, capable of determining the distraction force. A strain gauge or force transducer disposed on a portion of the interspinous process device 10 may also be used as an implantable feedback device. For example, the strain gauge may be able to communicate wirelessly the actual distraction force applied to the spine by the interspinous process device 10. A wireless reader or the like (that also can inductively power the strain gauge) may be used to read the distraction forces. One exemplary strain gauge sensor is the EMBEDSENSE wireless sensor, available from MicroStrain, Inc. of Williston, VT 05495. The EMBEDSENSE wireless sensor uses an inductive link to receive power form an external coil and returns digital stain measurements wirelessly.

In the embodiment of FIG. 8, the sensor 1084 is a microphone disposed on the external adjustment device 1130. For instance, the microphone sensor 1084 may be disposed in the recessed portion 1174 of the external adjustment device 1130. The output of the microphone sensor 1084 is directed to a signal processing circuit 1086 that amplifies and filters the detected acoustic signal. In this regard, the acoustic signal may include a "click" or other noise that is periodically generated by rotation of the hollow magnet 40. For example, the hollow magnet 40 may click every time a full rotation is made. The pitch (frequency) of the click may differ depending on the direction of rotation. For example, rotation in one direction (e.g., lengthening) may produce a low pitch while rotation in the other direction (e.g., shortening) may produce a higher pitch signal (or vice versa). Alternatively, rotation of the hollow magnet 40 in one direction (e.g., clockwise) may produce a relatively loud click while rotation in the opposite direction may produce a relatively quiet click. The amplified and filtered signal from the signal processing circuit 1086 can then pass to the PLC 1080. As an alternative to using a microphone sensor 1084 and associated circuitry, medical personnel may listen for the clicks using a stethoscope or similar instrument.

Additional details regarding the operation of various acoustic and other detection modalities may be found in U.S. patent application Ser. No. 12/121,355, published as U.S. patent application publication no. 2009/0112262, which is incorporated herein by reference.

During operation of the system 1076, each patient will have a number or indicia that correspond to the adjustment setting or size of their interspinous process device 10. This number can be stored on an optional storage device 1088 (as shown in FIG. 8) that is carried by the patient (e.g., memory card, magnetic card, or the like) or is integrally formed with the interspinous process device 10. For example, a RFID tag 1088 implanted either as part of the system or separately may be disposed inside the patient (e.g., subcutaneously or as part of the device) and can be read and written via an antenna 1090 to update the current size of the interspinous process device 10. In one aspect, the PLC 1080 has the ability to read the current number corresponding to the size or setting of the interspinous process device 10 from the storage device 1088. The PLC 1080 may also be able to write the adjusted or more updated current size or setting of the interspinous process device 10 to the storage device 1088. Of course, the current size may be recorded manually in the patient's medical records (e.g., chart, card or electronic patient record) that is then viewed and altered, as appropriate, each time the patient visits his or her physician.

The patient, therefore, carries their medical record with them, and if, for example, they are in another location, or even country, and need to be adjusted, the RFID tag 1088 has all of the information needed. Additionally, the RFID tag 1088 may be used as a security device. For example, the RFID tag 1088 may be used to allow only physicians to adjust the interspinous process device 10 and not patients. Alternatively, the RFID tag 1088 may be used to allow only certain models or makes of interspinous process devices to be adjusted by a specific model or serial number of external adjustment device 1130.

In one aspect, the current size or setting of the interspinous process device 10 is input into the PLC 1080. This may be done automatically or through manual input via, for instance, the keyboard 1083 that is associated with the PLC 1080. The PLC 1080 thus knows the patient's starting point. If the patient's records are lost, the length of the interspinous process device 10 may be measured by X-ray and the PLC 1080 may be manually programmed to this known starting point.

The external adjustment device 1130 is commanded to make an adjustment. This may be accomplished via a pre-set command entered into the PLC 1080 (e.g., "increase distraction displacement of interspinous process device 10 by 0.5 mm" or "increase distraction force of interspinous process device 10 to 20 pounds"). The PLC 1080 configures the proper direction for the motor 1132 and starts rotation of the motor 1132. As the motor 1132 spins, the encoder 1082 is able to continuously monitor the shaft position of the motor directly, as is shown in FIG. 8, or through another shaft or surface that is mechanically coupled to the motor 1132. For example, the encoder 1082 may read the position of markings 1177 located on the exterior of a pulley 1162C like that disclosed in FIG. 4. Every rotation or partial rotation of the motor 1132 can then be counted and used to calculate the adjusted or new size or setting of the interspinous process device 10.

The sensor 1084, which may include a microphone sensor 1084, may be monitored continuously. For example, every rotation of the motor 1132 should generate the appropriate number and pitch of clicks generated by rotation of the hollow magnet 40 inside the interspinous process device 10. If the motor 1132 turns a full revolution but no clicks are sensed, the magnetic coupling may have been lost and an error message may be displayed to the operator on a display 1081 of the PLC 1080. Similarly, an error message may be displayed on the display 1081 if the sensor 1084 acquires the wrong pitch of the auditory signal (e.g., the sensor 1084 detects a shortening pitch hut the external adjustment device 1130 was configured to lengthen).

While embodiments of the present invention have been shown and described, various modifications may be made without departing from the scope of the present invention. For example, the device can be used for treatment of various descriptions of the source of back pain: spondylolisthesis, degenerative spinal stenosis, disc herniations, instability, discogenic back pain, facet syndrome, and thecal sac changes to name a few. The invention, therefore, should not be limited, except to the following claims, and their equivalents.

What is claimed is:

1. A method comprising:

disposing an external adjustment device against a patient having an implant positioned below the surface of the patient's skin, a first mounting surface of the implant being attached to a first spinous process of a vertebral body and a second mounting surface of the implant being attached to a second spinous process of an adjacent vertebral body, the first mounting surface including a channel configured and dimensioned to receive the second mounting surface wherein the implant includes a magnetic assembly having a housing that terminates on one end with an O-ring gland having a recess configured to receive an O-ring, the O-ring configured to provide dynamic sealing within the housing;

noninvasively modifying a size of the implant with the external adjustment device positioned above the surface of the patient's skin such that a distance between the attached first and second spinous processes changes;

producing data based on the implant using a sensor of the external adjustment device, the sensor detecting an actual change in the implant size without contacting the implant; and determining a current modified size of the implant based on the produced data while the implant size is being modified.

2. The method of claim 1, wherein producing data based on the implant comprises:

passing a wave through the skin of the patient such that the wave reflects off a portion of the implant, the wave having a wavelength selected to be conducive for passage through tissue; and sensing the reflected wave with the sensor.

3. The method of claim 2, wherein the wave is a light wave; and wherein the sensor is a photodetector.

4. The method of claim 1, wherein producing data based on the implant includes detecting a sound generated by the implant.

5. The method of claim 4, wherein producing data based on the implant includes periodically detecting the sound generated by the implant.

6. The method of claim 4, further comprising:

detecting a first sound produced by the implant being modified in a first way; and detecting a second sound produced by the implant being modified in a second way.

7. The method of claim 6, wherein the first sound has a higher frequency than the second sound.

8. The method of claim 6, wherein the first way is lengthening and the second way is shortening.

9. The method of claim 1, further comprising reading from a storage device of the implant using the external adjustment device.

10. The method of claim 9, further comprising limiting a functionality of the external adjustment device based on the reading from the storage device of the implant.

11. The method of claim 9, wherein reading from the storage device of the implant includes reading a specified model;

comparing a model of the external adjustment device with the specified model; and limiting functionality of the external adjustment device based on the comparison.

12. The method of claim 9, further comprising writing to the storage device of the implant using the external adjustment device.

13. The method of claim 1, further comprising:

comparing the produced data to an expected result; and providing an error message based on the comparison.

14. The method of claim 13, further comprising:

sensing movement of a component of the external adjustment device; and determining the expected result based on the sensed movement.

15. The method of claim 1, wherein disposing the external adjustment device against the patient includes:

placing the external adjustment device against clothing of the patient, wherein modifying the implant occurs through the clothing of the patient.

16. The method of claim 1, wherein disposing the external adjustment device against the patient includes:

magnetically coupling at least one external magnet of the external adjustment device with at least one implanted magnet of the implant.

17. The method of claim 1, wherein modifying the implant with the external adjustment device includes:

lengthening the implant;

shortening the implant;

increasing a distraction force of the implant; or decreasing the distraction force of the implant.

* * * * *